(12) United States Patent
Bronnert

(10) Patent No.: US 10,563,935 B2
(45) Date of Patent: Feb. 18, 2020

(54) ASEPTIC HIGH TEMPERATURE HEAT EXCHANGER INSPECTION SYSTEM

(71) Applicant: Herve' X. Bronnert, Brookfield, WI (US)

(72) Inventor: Herve' X. Bronnert, Brookfield, WI (US)

(*) Notice: Subject to any disclaimer, the term of this patent is extended or adjusted under 35 U.S.C. 154(b) by 284 days.

(21) Appl. No.: 15/449,936

(22) Filed: Mar. 4, 2017

(65) Prior Publication Data
US 2017/0254603 A1 Sep. 7, 2017

Related U.S. Application Data

(60) Provisional application No. 62/303,744, filed on Mar. 4, 2016.

(51) Int. Cl.
*F28F 19/00* (2006.01)
*F28F 27/00* (2006.01)
*G01N 21/94* (2006.01)
*G01N 21/954* (2006.01)

(52) U.S. Cl.
CPC ............. *F28F 27/00* (2013.01); *G01N 21/94* (2013.01); *G01N 21/954* (2013.01); *G01N 2021/9542* (2013.01)

(58) Field of Classification Search
CPC .. F28F 5/00; F28F 27/00; F24H 1/403; B01D 1/305; B05B 12/08; G01N 21/94; G01N 21/954; G01N 2021/9542
USPC .................................... 165/11.1; 239/71, 74
See application file for complete search history.

(56) References Cited

U.S. PATENT DOCUMENTS

| | | | |
|---|---|---|---|
| 6,622,934 B1* | 9/2003 | Sanada | B05B 12/08 239/102.2 |
| 2009/0218210 A1* | 9/2009 | Demmons | B01D 1/305 203/22 |
| 2011/0203781 A1* | 8/2011 | Ellingwood | F24H 1/403 165/173 |
| 2014/0110094 A1* | 4/2014 | Pagan Duran | F28F 5/00 165/172 |

* cited by examiner

*Primary Examiner* — Davis D Hwu
(74) *Attorney, Agent, or Firm* — Rathe Lindenbaum LLP

(57) ABSTRACT

An inspection system for a heat exchanger having a vision system to obtain an image of an inner surface of the at least one tube.

9 Claims, 4 Drawing Sheets

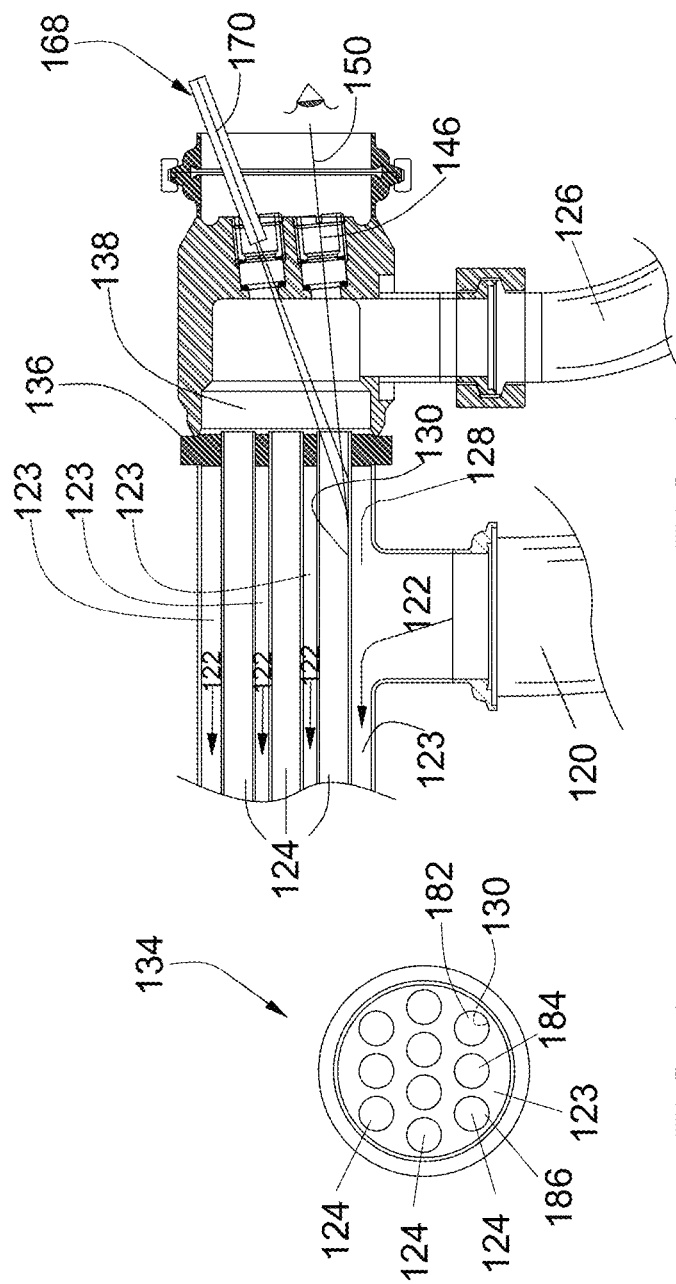

ASEPTIC HIGH TEMPERATURE HEAT EXCHANGER INSPECTION SYSTEM

CROSS-REFERENCE TO RELATED PATENT APPLICATIONS

This application claims the benefit of U.S. Provisional Application No. 62/303,744 filed on Mar. 4, 2016 and entitled HEAT EXCHANGER INSPECTION SYSTEM the entirety of which is incorporated herein by reference.

BACKGROUND

The present invention relates generally to the field of heat exchangers and more particularly, to a system for inspecting the inner surfaces of a heat exchanger found on a tubular aseptic or high temperature system for processing low acid products.

Low acid products, such as, milk, cream, ice cream mix, nutritional drinks, dairy alternative drinks, puddings, cheese sauce, soups, dips and sauces are susceptible to the formation of deposit on the heating surface during processing. The formation of deposit which denatures with time and temperature become "burn-on". This is a common problem found on any aseptic processing system, when a tubular aseptic or high temperature system is engineered to resist burn-on. This invention enables inspection of the inner surfaces of the heat exchanger at the critical point where deposit might occur in case of any or accidental or undesirable event.

BRIEF DESCRIPTION OF THE DRAWINGS

FIG. 2 is a cross section of a portion of the heat exchanger of FIG. 1.

FIG. 3 is a partial cross section of an inspection system for a heat exchanger system with manual inspection.

DETAILED DESCRIPTION OF THE EXAMPLE EMBODIMENTS

Figure 4:
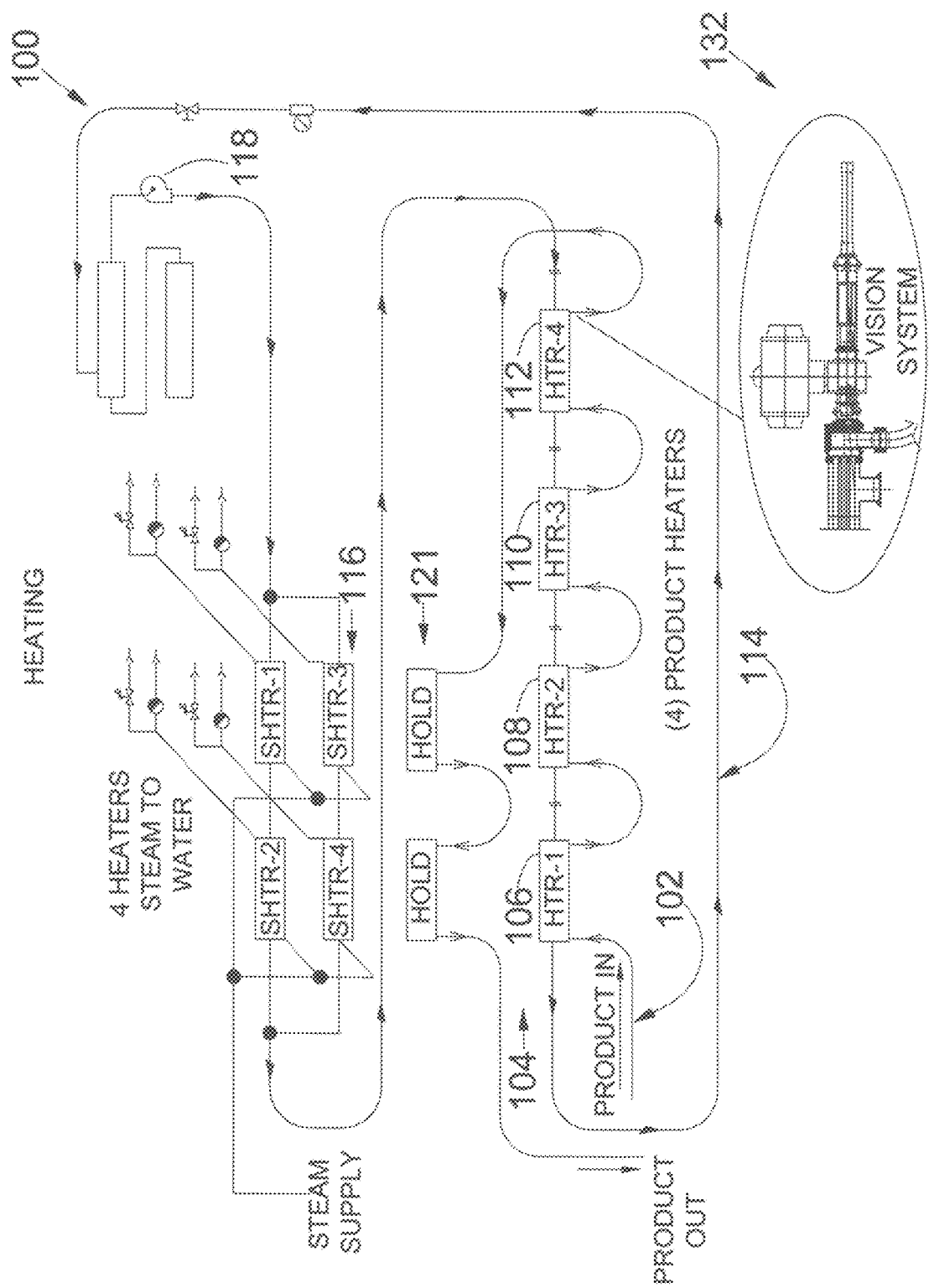
FIG. 4 is a schematic view of a heat exchanger with an inspection system.

Referring to FIG. 4 in one embodiment a heat exchanger 100 for processing food product includes a first path 102 for moving a food product through a series of heat exchangers 104. In one embodiment product is pumped through a first heat exchanger 106, a second heat exchanger 108, a third heat exchanger 110 and a fourth heat exchanger 112. However, the number of heat exchangers may be fewer than four or greater than four.

In a second path 114, heated water is pumped by pump 118 through a series of steam heaters 116 until the temperature of the water is raised to the desired temperature. In one embodiment, the temperature of the water in the second path is about 290 deg. F. The heated water is pumped by pump 118 under pressure through each of the heat exchangers 106, 108, 110 and 112. In one embodiment heat exchanger 112 is the last heat exchanger before the food product being processed is transferred to a holder or container 120. The hot water being pumped through the second path 114 flows in a direction opposite to the direction of the flow of the food product. Accordingly, in one embodiment the temperature of the water will be slightly hotter in the last heat exchanger 112 than in the first heat exchanger 104. Note that the last heat exchanger 112 is the last opportunity for the food product to be heated. The first heat exchanger 106 is the first time that the food product in the first path 102 is being heated by the hot water.

Figure 1:
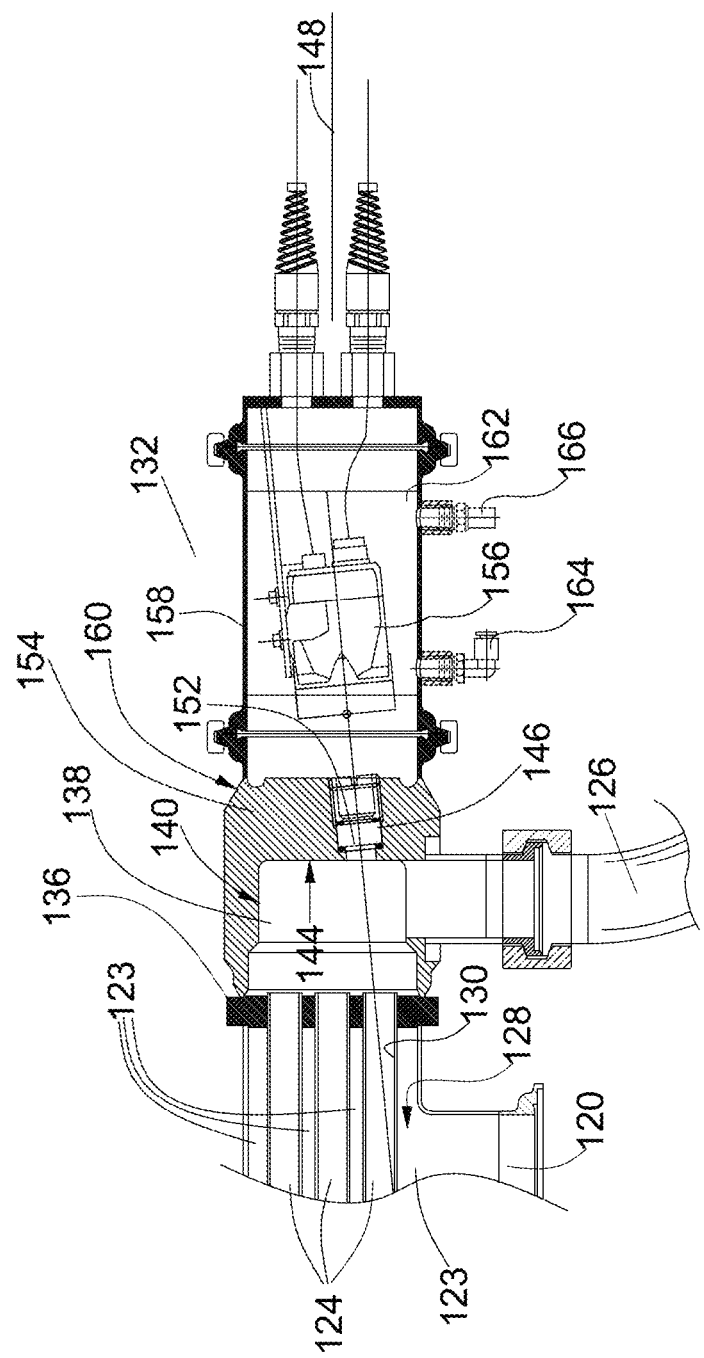
FIG. 1 is a partial cross section of an inspection system for a heat exchanger system.

Since the water will be hottest when the hot water enters heat exchanger 112 this is the area where one would expect there to be a deposit of the food product or burn on if any. Referring to FIG. 1 and FIG. 2 the hot water enters each heat exchanger through connection 121 and flows in a direction 122 around the tubes 124 in region 123 thereby heating the food product. The food product flows in a direction opposite to direction 122 of the hot water flow and exits the heat exchanger via conduit 126. The region 128 of tubes 124 is the area in which the hot water first contacts the tubes 124 in the direction that the hot water flows. The water will be hottest at this point since it will be transferring the heat from the water to the food product through the heat exchangers. Accordingly, region 128 in the last of the heat exchangers will be heated to the highest temperature of all the heat exchangers. It is believed that region 128 in which the hot water enters heat exchanger 112 is the hottest that the water will be in all the heat exchangers and therefore the region in which tubes 124 will reach the highest temperature during the heat transfer process. Region 128 of the last heat exchanger 112 is where the hot water first begins to transfer heat to the food product and it is the location in which the food product is last heated. Accordingly, region 128 is the location where a deposit or burn on is likely to take place if it is going to be anywhere within the system. Inspection of the heat exchanger system at this location for any food deposit or burn on can be identified before further processing the tubular aseptic or high temperature system for processing low acid products. If there is no deposit or burn on in the last heat exchanger 112 then there is likely to be no deposit or burn on anywhere in the system.

Referring to FIG. 1 and FIG. 2 heat exchanger 112 includes an outer housing tube member 134 defining an internal region 123 through which the hot water flows around the plurality of inner tubes 124. The hot water enters the region 123 of outer tubing member 134 via an inlet port 120. Outer housing tube member 124 includes a tube sheet member 136 at a terminal end of the outer tubing member that prevents water from entering the product outlet region 138 which is defined by structure 140 having a terminal end wall 144 defining a product contact surface 144. Extending from structure 140 is food product outlet 126 through which food product exits the heat exchanger.

To avoid confusion the term last heat exchanger refers to the last of the heat exchangers through which the food product is heated in the direction that the food product flows through the first path. The last heat exchanger is the heat exchanger that the hot water first enters along the second path that flows opposite to the first path.

In one embodiment, the tubular aseptic or high temperature system processing for low acid products allows for inspection of the inner surface 130 of the inner tubes 124 of a tubular heat exchanger without operator manual intervention. Inner surfaces 130 is the surface of the tubes 124 that directly contact the food product that is being pumped through the tubes 124. In one embodiment, an automatic optical/electronic photographic system 132 connected to a PLC and operator interface or equivalent such as a digital display allows the display of the inside surface 130 of inner tubes 124 of the first path to allow for surface inspection of the inside surfaces 130 of at least one of the heat exchangers. A PLC as used herein is a programmable logic controller that includes a digital processor that through software instructions obtains the digital image from the digital camera and transfers the image data to the display. The PLC may also open and close a valve and move the housing supporting the digital camera as explained herein below. In one embodiment, a user does not need to disassemble any portion of the first path to allow internal viewing of the inner surface 130 of the tubes 124 in the first path 102 through which the food product travels.

Inspection takes place where the heating media comes in, generating the maximum temperatures difference where more deposit is likely to form and deposit and burn on occur. The inspection of the heat exchange tube inside surface is when the system is filled with clear and clean water. This is after CIP (clean-in-place) and after final when the tubular processing system is standing without flow. In one embodiment inspection of the internal surface 130 of the tubular members 124 of path 102 is conducted after the tubes 124 have been cleaned and are filled with clear clean water.

A transparent mounting assembly 146 is secured to the contact surface 144 of structure 140 to optically couple the transparent mounting assembly 146 to the product outlet region 138 of structure 140. Transparent mounting assembly 146 allows for the inspection of the surface 130 of at least one inner tube 124 in region 128 of the heat exchanger. Heat exchanger 112 includes a longitudinal axis 148 that extends the length of the heat exchanger tubes and is centrally located within tubular housing 134. Transparent mounting assembly 146 has a longitudinal axis 150 that that is not concentric and not parallel to the longitudinal axis 146 of the heat exchanger. Longitudinal axis 150 is set to intersect surface 130 of one of the tubes 124 in region 128. In one embodiment, the tube 124 that longitudinal axis 150 intersects is one of the inner tube 124 that is closest to inlet 120 of the hot water.

A transparent member 152 separates an aseptic reducer 154 that defines structure 140 to allow a vision sensor 156. Vision sensor may include a digital camera to obtain images of the inner surface 130 of a tube 124 in region 128. Vision sensor 156 may also include a light source to illuminate the inner surface 130 to allow the digital camera to obtain an image of the inner surface 130 that may be transmitted to a digital display for visual examination by a user.

Referring to FIG. 1 inspection system 132 includes a housing 158 that is removably coupled to the aseptic reducer 160 which allows the installation of a high temperature transparent "window" 152 in line with the heat exchanger end tubing. In one embodiment, the high temperature transparent window may be formed materials that withstand the high temperatures of 290 degrees F. that are known in the art are also contemplated. This "window" is tilted to allow inspecting the internal surface of the tubes at an angle. A chamber 162 with air cooling is formed to place in line with the window and autofocus vision sensor which takes a picture transferred to a PLC display. This sensor has its own illumination to take pictures in this dark setting. The housing 158 may be disconnected or opened for any mounting and servicing of the vision sensor 156 that may be needed.

Referring to FIG. 1 chamber 162 is cooled with air that enters through inlet port 164 and exits through outlet port 166. The air may air have a temperature that is less than the temperature of the hot water being pumped through second path 114.

Referring to FIG. 3, a manual inspection port 168 may extend through housing 158 to allow an operator to view the inner surface 130 of tube 124 without the use of a digital camera or in addition to the use of a digital camera. The line of sight of the manual inspection port 168 extends along a longitudinal axis 170 that intersects the inner surface 130 of at least one tube 124. The manual inspection port 168 in one embodiment has its own illumination light source to light up the internal surface 130 of tube 124. The longitudinal axis 170 is non-parallel to and non-coincident with the longitudinal axis 148 of heat exchanger 112. In one embodiment, the only inspection port is the manual inspection port 168. However, in one embodiment manual inspection port 168 is in addition to digital transparent mounting assembly 146. In this embodiment, the manual inspection port may be used in conjunction with or independently of the digital inspection port 146. In the embodiment in which there is both the manual inspection port that allows a user to view through a conduit the inner surface 130 of tube 124 in region 128 as well as the digital transparent mounting assembly 146 the longitudinal axis 170 is not parallel to or coincident with the longitudinal axis 150 of the assembly 146. Additionally, in one embodiment longitudinal axis 170 intersects surface 130 at the same point as longitudinal axis 150 intersects surface 130. In this manner, it is possible to directly view surface 130 at the same point as the digital display showing the digital image from the digital camera 156.

In one embodiment, longitudinal axis 170 intersects surface 130 at a different same point than the intersection point of longitudinal axis 150 and surface 130. In this manner, it is possible to observe different areas on surface 130 of tube 124.

Figure 5:
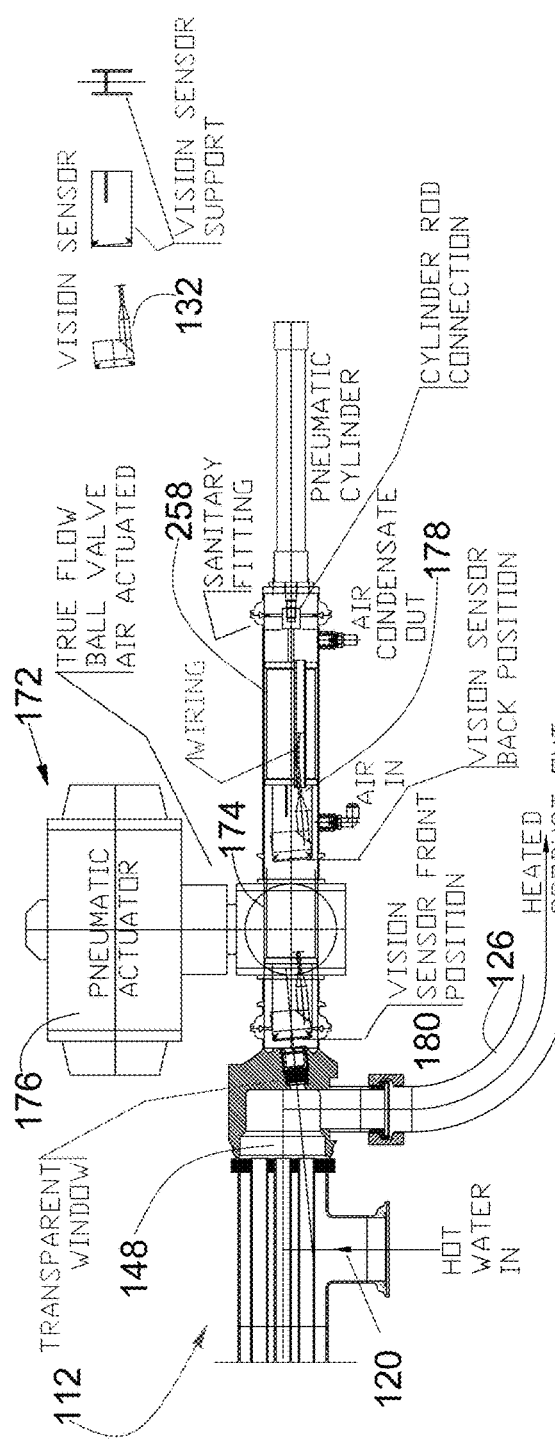
FIG. 5 is a partial cross section of a movable inspection system for a heat exchanger system.
Figure 6:
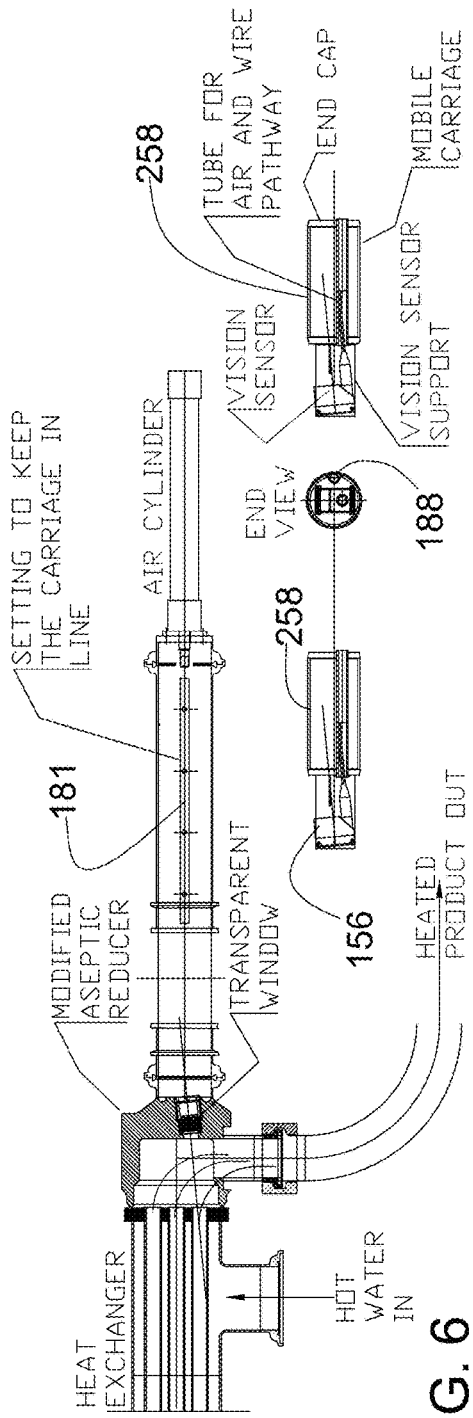
FIG. 6 are other views of the movable inspection system of FIG. 5.

Referring to FIG. 5 vision system 132 includes a heat shield system 172 that provides a thermal and radiation shield between heat exchanger 112 and vision system 132. Heat shield system 172 includes a ball valve 174 being movable between a closed position and an open position. In closed position the ball valve is positioned such that the region between a housing or also referred to herein as a movable carriage 258 and heat exchanger 112 is blocked by the ball valve. In the open orientation of the ball valve the valve is in the open position allowing at least a portion of movable carriage 258 to extend there through to move the digital camera in to the position in which a digital image of the inner surface 130 may be obtained. The movement of the valve between the open position and closed position may be accomplished with an actuator 176 that may be automatically opened and closed in coordination with the movement of movable carriage 258 and the taking of the digital pictures of surface 130. As in the non-moving housing embodiment illustrated in FIG. 1 and FIG. 3 and discussed above, movable carriage 258 has an air cooling system in which air enter inlet 164 and exits outlet 166 to cool the chamber 162 while the digital camera is in the in-use position. Movable carriage 258 in this embodiment is moved along its longitudinal axis between an in-use position and a retracted position through the ball valve by a pneumatic drive. However other drive mechanisms are contemplated. In one embodiment, the movement of the ball valve, movement of movable carriage 258 and the capture of the image of surface 130 by digital camera are all automated through a series of steps by directions from a controller. Referring to FIG. 5 container 258 is shown in a withdrawn position at position 178 and in an in-use position 180. Movable carriage 258 supports a digital camera 156. In all other respects movable carriage 258 and digital camera 156 operate as described above with respect to FIG. 1 and FIG. 3. The in-use position 180 is a front position in which digital camera 156 is in position to obtain an image of surface 130. The non in-use position or retracted position 178 may also be referred to as a rear position.

Movable carriage 258 in one embodiment extends along a rail 181 within a groove 188 to help provide proper alignment of digital camera 156.

In one embodiment, digital camera 156 has a field of view that captures the inner surface 130 of more than one tube 124. Referring to FIG. 2, digital camera 156 in one embodiment captures the inner surfaces 130 of tubes 182, 184, 186 all of which have been commonly referred to as tube 124. As used herein tube 124 can be understood to describe an individual tube or more than one tube.

In one embodiment, the vision sensor provides automatic focusing and exposure time and illumination are adjusted automatically. The camera adjusts and stabilizes the LED light illuminating the internal surface area of the inner tubes of a heat exchanger. A heat exchanger may have one or more inner tubes. The vision sensor illuminates the targeted area to take a picture, transfer it to the PLC using Ethernet then the PLC transfers it to an operator interface for showing the pictures on a screen such as a digital display screen.

The vision camera is set at a specific angle with the tube's internal diameter to see if a deposit has formed. If a deposit has formed, another clean in place operation with caustic and acid must be done. After doing another CIP, the internal diameter of the tubes are reexamined using the vision sensor to confirm that the tubes are free of deposit before processing. To be free of deposit can increase productivity, product quality and flavor.

Further modifications and alternative embodiments of various aspects of the invention will be apparent to those skilled in the art in view of this description. Accordingly, this description is to be construed as illustrative only. The construction and arrangements, shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The features described herein may be combined in any combination and such combinations are contemplated. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

What is claimed is:

1. An apparatus comprising:
    a heat exchanger having a single or plurality of inner tubes located within an outer tube having a defining a longitudinal axis;
    a housing adjacent the heat exchanger including a transparent member, the housing including a view port having a view port longitudinal axis that is non-parallel and non-coincident with the longitudinal axis of the heat exchanger;
    the view port longitudinal axis intersecting an internal surface of the at least one inner tube; and
    a light source illuminating the internal surface.

2. The apparatus of claim 1, wherein the view port has a proximal end configured to allow an operator to view the inner surface of the inner tube therethrough.

3. The apparatus of claim 1 further including a digital camera having a field of view along the view port longitudinal axis and obtaining an image of the inner surface of the inner tube.

4. The inspection system of claim 3 further including a mobile carriage supporting the camera.

5. The inspection system of claim 4, wherein the mobile carriage moves from a first in use position to a second non in-use position.

6. The inspection system of claim 5, further including a valve movable form a closed orientation to an open orientation, wherein a portion of the mobile housing moves through the valve as the mobile carriage is moved from the non in-use position to the in-use position, the mobile carriage being in the in-use position when the valve is in the open orientation and in the non in-use position when the valve is in the closed orientation.

7. The inspection system of claim 6, wherein the housing includes an inlet for receiving air and an outlet for venting the air, wherein the air has a temperature less than the temperature of the camera.

8. The inspection system of claim 3, wherein the camera is a digital camera having a field of vision that captures an image of one or more than one tube in the heat exchanger at one time.

9. The apparatus of claim 3, further including a second view port having a longitudinal axis that is non-parallel to the view portion longitudinal axis, the view port having a proximal end providing a field of view of the inner surface of the inner tube to an operator without the need for a camera.

* * * * *